(12) United States Patent
Bowen et al.

(10) Patent No.: US 7,610,918 B2
(45) Date of Patent: Nov. 3, 2009

(54) SURGICAL DRAPE WITH AN INTEGRAL UNDERBUTTOCKS PORTION

(75) Inventors: Uyles W. Bowen, Canton, GA (US); Patricia Pyeatt-Rowe, Alpharetta, GA (US); Andrea L. Lewis, Mount Pleasant, SC (US); Gwendolyn E. Simpson, Riverdale, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 470 days.

(21) Appl. No.: 11/192,441

(22) Filed: Jul. 28, 2005

(65) Prior Publication Data
US 2007/0023053 A1    Feb. 1, 2007

(51) Int. Cl.
A61B 19/00    (2006.01)
A61B 19/08    (2006.01)

(52) U.S. Cl. .................. 128/849; 128/850; 128/851; 128/852; 128/853

(58) Field of Classification Search .......... 128/849–855
See application file for complete search history.

(56) References Cited

U.S. PATENT DOCUMENTS

| | | | | |
|---|---|---|---|---|
| 3,797,484 A | | 3/1974 | Ericson | |
| 3,809,077 A | * | 5/1974 | Hansen | 128/849 |
| 3,856,006 A | * | 12/1974 | Krzewinski | 128/852 |
| 3,942,523 A | | 3/1976 | Rudtke | |
| 5,388,593 A | | 2/1995 | Thomalla | |
| 5,445,165 A | * | 8/1995 | Fenwick | 128/849 |
| 5,471,999 A | * | 12/1995 | Mills | 128/849 |
| 5,709,221 A | | 1/1998 | Vancaillie et al. | |
| 5,988,172 A | | 11/1999 | Sosebee | |
| 5,991,666 A | | 11/1999 | Vought | |
| 6,055,987 A | | 5/2000 | Griesbach et al. | |
| 6,314,958 B1 | | 11/2001 | Harroll et al. | |
| 2003/0188753 A1 | | 10/2003 | Jascomb | |

OTHER PUBLICATIONS

PCT Search Report—Nov. 6, 2006.

* cited by examiner

*Primary Examiner*—Michael Phillips
*Assistant Examiner*—Tarla R Patel
(74) *Attorney, Agent, or Firm*—Dority & Manning, P.A.

(57) ABSTRACT

A surgical drape for use during surgery on a patient includes a sheet configured for covering at least a portion of the patient during the surgery. The drape includes a first sheet portion having a size and configuration to overlie the patient during the medical procedure. A fenestration is defined in the first sheet portion at a location corresponding to the site of the medical procedure on the patient. A second sheet portion is attached to a lower surface of the first sheet portion and has a size and configuration so as to be draped from the first sheet portion and extend under the patient's buttocks while remaining attached to first sheet during the medical procedure.

12 Claims, 6 Drawing Sheets

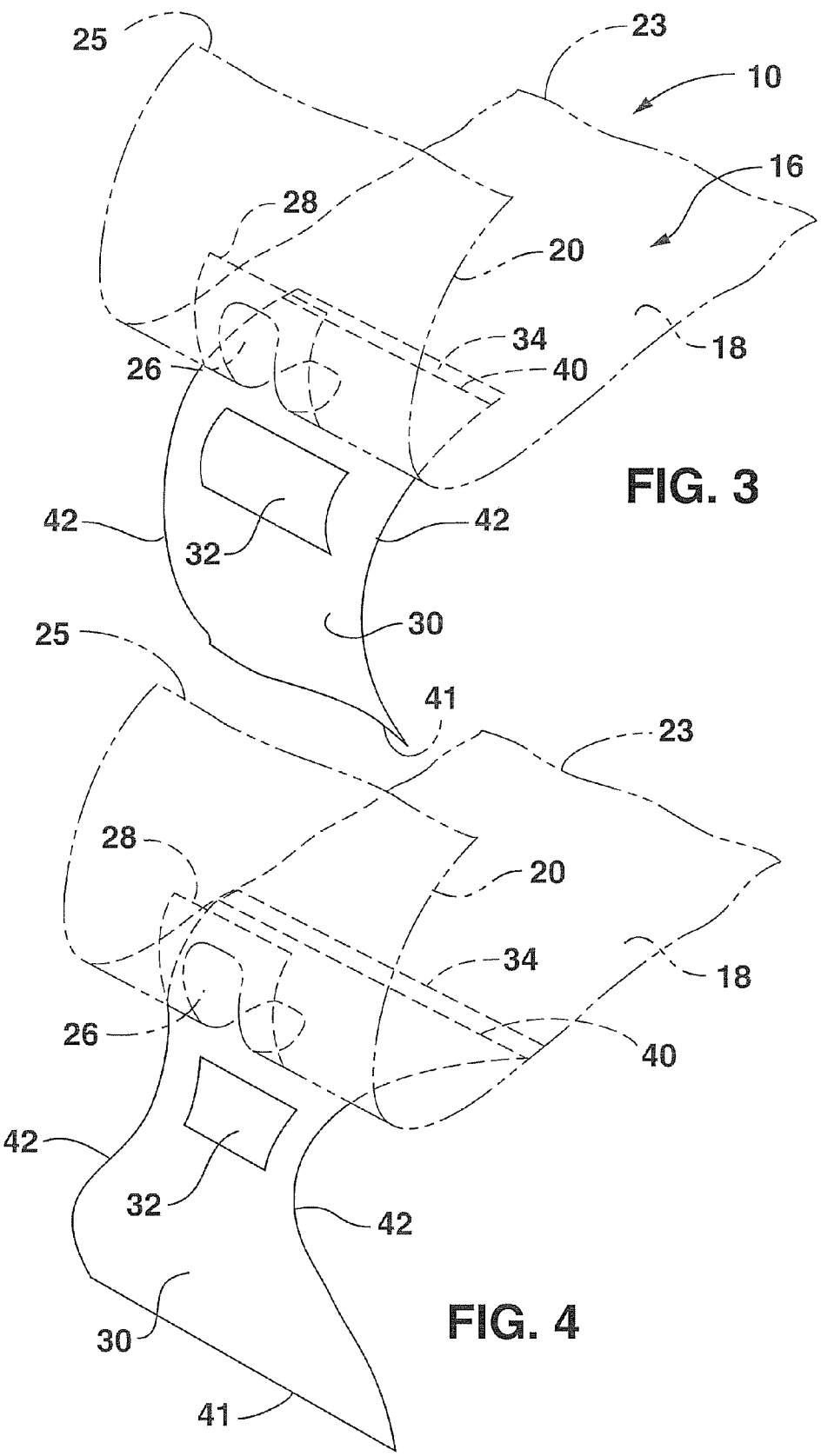

SURGICAL DRAPE WITH AN INTEGRAL UNDERBUTTOCKS PORTION

BACKGROUND

Various types of surgical drapes are known and used to keep a surgical site on a patient sterile during a surgical procedure. Traditionally, surgical drapes were linen or woven cloth, and were sterilized after each use for reuse. More recently, disposable sterile drapes have been introduced, in which a nonwoven paper or fabric forms a substantial part of the drape.

Various surgical procedures and examinations, especially urological, gynecological, proctological, and perineal procedures in general, require the patient to be disposed in the Lithotomy position. A surgical drape is placed over the patient with leg covering portions overlying the patient's legs, which are mounted in stirrups. A central, downwardly extending portion of the drape extending between the patient's legs is provided with a fenestration through which the surgeon performs a particular procedure. The patient facing surface of the drape surrounding the fenestration may include an adhesive for attaching the drape directly to the patient.

With many of the noted procedures, a relatively large quantity of fluid is often introduced to and/or output from the patient. It is often necessary to closely monitor this fluid quantity, and it is know in the art to use various pouch configurations to collect the fluid. It is common, however, that fluid leakage occurs between the overlaying drape and the patient resulting in fluid run-off onto the operating table and floor of the operating room. This fluid may also result in various undesirable conditions for the patient in that it accumulates on the operating bed under the patient and the patient remains in contact with the fluid for the duration of the procedure.

In an attempt to alleviate potential problems from fluid run-off and collection under the patient, it is a practice to place a separate drape under the patient's buttocks prior to the sterile field draping procedure, with this drape hanging over the end of the operating table where the procedure is performed. This procedure, however, is time consuming and requires multiple drapes and a multiple step donning process with multiple personnel.

U.S. Pat. No. 6,314,958 describes an underbuttocks drape for controlling fluid reaching a buttocks area of a patient. This drape is a separate component from the sterile field drape and includes a base sheet that is positioned on the operating table under the patient's buttocks. A sealing lip is attached to the base sheet and circumscribes at least a portion of the sheet positioned under the buttocks. The sealing lip includes a compressible foam construction adapted to conform to a contour of the patient around the buttocks as the patient rests on the base sheet. The sealing lip is adapted to fill gaps between the base sheet and the patient such that fluid running along the buttocks is caused to drain into a fluid collection pouch. With this system, however, the underbuttocks sheet must still be separately placed below the patient prior to donning of the sterile surgical drape.

A need thus still exists in the art for a more versatile surgical drape and associated donning procedure that incorporates an underbuttocks drape.

SUMMARY

Various features and advantages of the invention will be set forth in the following description, or may be obvious from the description, or may be learned from practice of the invention.

In accordance with various aspects of the invention, a surgical drape is provided for use during any manner of medical procedure on a patient wherein it is desired to use an underbuttocks drape in addition to a sterile field drape. The drape includes a first sheet portion having a size and configuration to overlie the patient during the medical procedure, the first sheet portion having an upper surface and a patient facing lower surface. The first sheet portion may be configured according to any manner of conventional drape configuration know in the art for use in any perineal procedure, especially urological, gynecological, and proctological procedures. A fenestration is defined in the first sheet portion at a location corresponding to the site of the intended medical procedure on the patient. The fenestration may be of any conventional design and may include a reinforcement panel surrounding the fenestration opening, as is know in the art.

A second sheet portion is attached to the lower surface of the first sheet along an attachment axis by any conventional means, including adhesive, bonding, stitching, and so forth. The second sheet portion has a size and configuration so as to be draped from the first sheet, extend between the patient's legs, and extend under the patient's buttocks while remaining attached to first sheet during the medical procedure. In a particular embodiment, the second sheet portion is attached to the first sheet portion at a location above the fenestration (towards the patient's head). In this embodiment, it should be understood that the medical procedure is performed through an opening in the second sheet portion. This opening may be, for example, a hole having any desired shape. In an alternate embodiment, the access opening may be defined by a perforation line or pattern in the second sheet portion that is opened by the medical staff after donning of the drape and prior to the procedure. In still an alternate embodiment, the access opening may simply be cut into the second sheet portion by the medical staff prior to the procedure.

The drape according to the invention is not limited in any regard by the materials used to construct the various drape portions. It may be desired that the first and second sheet portions be made of the same materials, or different materials. In one embodiment, the second sheet portion includes a liquid impermeable material. For example, the second sheet portion may be formed of a laminate of an absorbent sheet material and a liquid impermeable material, with the liquid impermeable material disposed outwardly facing and the absorbent material defining the patient facing surface of the sheet portion.

The second sheet portion may have various shapes and configurations relative to the first sheet portion. For example, the second sheet portion may be generally rectangular with a width generally equal to that of the first sheet portion. In this embodiment, the second sheet portion may be attached to the first sheet portion generally along the entire width of the respective sheet portions. In an alternate embodiment, the second sheet portion has a width less than that of the first sheet portion and is centered relative to first sheet portion.

The second sheet portion may have a contoured configuration designed to reduce bunching of the sheet portion at the location between the attachment axis of the second sheet portion and the patient's buttocks. For example, the second sheet portion may have a tapered diverging shape, or a generally hour-glass shape. Various shapes are contemplated for better accommodating the patient's legs and buttocks without causing undue bunching of the second sheet portion material.

As with all conventional drapes, the unique surgical drape according to the invention is provided in a packaged and stowed configuration prior to donning. With its unique configuration, the drape according to the invention is folded so as to be donned in a single step with minimal medical personnel involvement. In a particular configuration, a first section of the first sheet portion is folded from a first end (patient head end) towards the attachment axis of the second sheet portion, and a second section is folded from the opposite towards the attachment axis. The second sheet portion (underbuttocks portion) is preferably rolled towards the attachment axis. Rolling of the second sheet portion may be desired in that it can be subsequently unrolled by placing one's hand and arm within the roll, with the hand and arm remaining covered and sterile during the donning procedure. Thus, the drape contains three distinct sections in its stowed configuration sharing a common axis at the attachment axis of the second sheet portion. The sections may then be folded or rolled into a compact reduced width package.

To don the drape, the patient is placed in the Lithotomy position and the drape is unfolded or unrolled in the width (lateral) direction across the patient. The first folded section of the first sheet portion is then unfolded from the attachment axis across the patient's torso towards the patient's head. The second sheet portion (the underbuttocks portion) is then unrolled from the attachment axis and placed below the patient's buttocks. If necessary, access through the second sheet portion may be defined at this time, for example by cutting an opening through the sheet material, or separating the material along a predefined perforation line. The second folded section of the first sheet material portion is then unfolded for placement of the leggings and perineal fenestration.

Additional aspects of the invention will be described below by reference to particular embodiments illustrated in the figures.

BRIEF DESCRIPTION OF THE DRAWINGS

FIG. 3 is a perspective view of an alternative embodiment of the underbuttocks portion of the drape.

FIG. 4 is a perspective view of still another embodiment of the underbuttocks portion of the drape.

DETAILED DESCRIPTION

Figure 1:
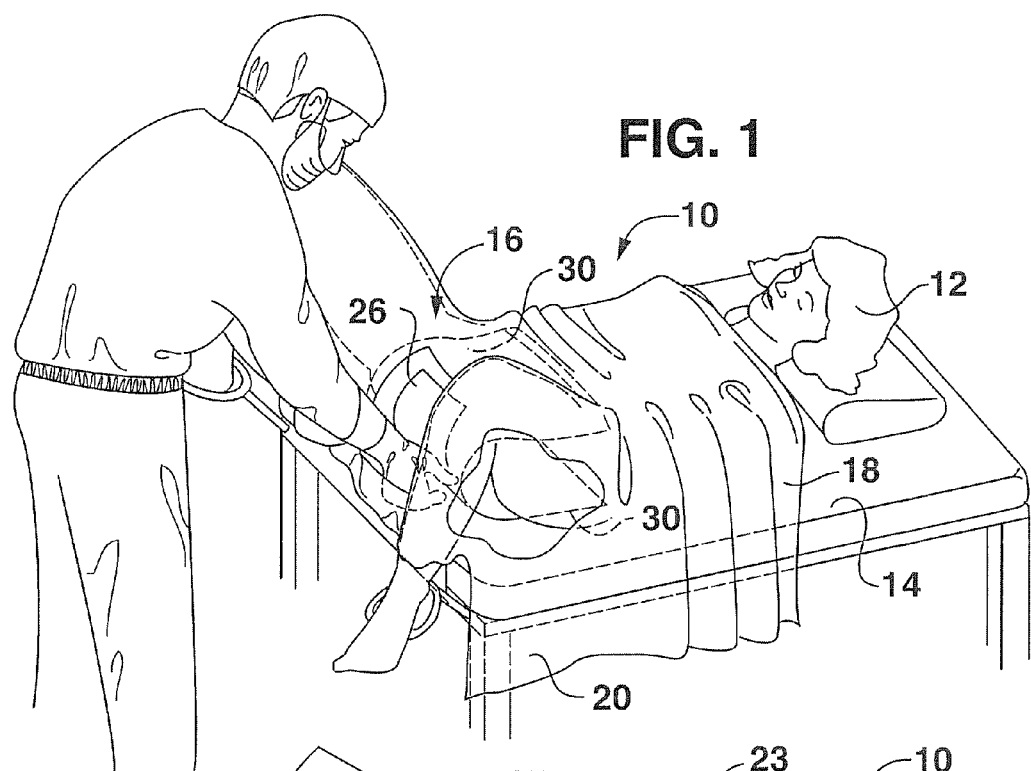
FIG. 1 is a perspective view of an exemplary embodiment of a surgical drape in accordance with the present invention.

Reference will now be made in detail to one or more embodiments of the invention, examples of which are graphically illustrated in the drawings. The embodiments are provided by way of explanation of the invention, and not meant as a limitation of the invention. For example, features illustrated or described as part of one embodiment may be utilized with another embodiment to yield still a further embodiment. It is intended that the present invention include these and other modifications and variations.

As used herein, "attach" or "attached" refers to the bonding, joining, adhering, connecting, attaching, or the like, of two elements. Two elements may be considered attached together when they are bonded directly to one another or indirectly to one another, such as when each is directly attached to an intermediate element.

"Nonwoven web" refers to a web that has a structure of individual fibers or filaments that are interlaid, but in an identifiable repeating manner. Nonwoven webs or fabrics have been formed from many processes known to those skilled in the art, such as meltblowing processes, spunbonding processes, bonded carded web processes, and so forth. The basis weight of nonwoven fabrics is usually expressed in ounces of material per square yard (osy) or grams per square meter (gsm), and the fiber diameters are usually expressed in microns.

Surgical drapes formed in accordance with the present invention can generally possess any of a variety of sizes and shapes, depending on the particular use of the drape and its desired properties. For example, certain surgical drape configurations are described in U.S. Pat. No. 6,055,987, which is incorporated herein by reference for all purposes. Features of conventional drapes are discussed generally herein, but need not be described in detail for a complete understanding of drapes incorporating the novel underbuttocks portion according to the invention.

Figure 2:
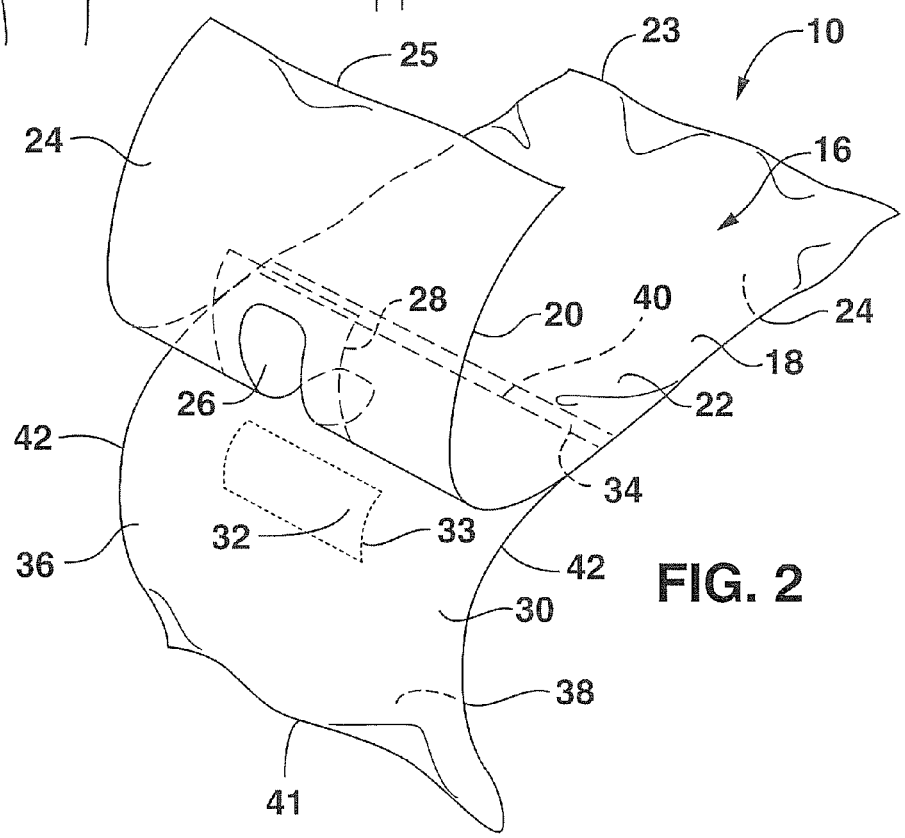
FIG. 2 is a perspective view of the exemplary embodiment of FIG. 1 particularly illustrating the different drape portions.

Referring to FIGS. 1 and 2 in general, an embodiment of a surgical drape 10 according to the invention is illustrated. The drape 10 is configured for use during any manner of medical procedure on a patient 12 wherein it is desired to use an underbuttocks drape in addition to a sterile field drape. The drape 10 includes a base sheet material defining a first sheet portion 16 having a size and configuration to overlie the patient 12 during the medical procedure. The first sheet portion 16 has an upper surface 22 (facing away from the patient) and a lower surface 24 (facing towards the patient). The first sheet portion 16 may be formed from one or more materials, for example one or more nonwoven layers, adhesive layers, film layers, and so forth. The first sheet portion 16 may be hydrophilic or hydrophobic, and can be chemically treated to achieve desired water absorbency properties. In a particular embodiment, the first sheet portion 16 is a nonwoven surface layer joined to a barrier layer by a meltblown adhesive layer. The nonwoven surface layer may be a spunbond propylene material sheet with a basis weight of about 20 gsm bonded by a repeating pattern of discretely fused spaced apart bonds. The meltblown adhesive layer may be an amorphous polyolefin applied to the spunbond material at a rate of, for example, 3 gsm. The barrier layer may be a polyethylene and calcium carbonate film of about 1.5 mils thick. The film may be stretched in one direction prior to lamination to the spunbond material by the meltblown adhesive layer. The film provides an impermeable barrier to aqueous fluids and alcohol solutions; the inclusion of the calcium carbonate and subsequent stretching improving moisture vapor permeability.

The first sheet portion 16 may correspond to any manner of conventional drape configuration known in the art for use in any perineal procedure, especially urological, gynecological, and proctological procedures.

The drape 10 may include a fenestration opening 26 that is placed over the surgical site such that the surgical procedure is performed through the fenestration 26. The fenestration can have any desired shape and dimensions. A separate material panel 28 may be attached to the first sheet portion 16 around the fenestration 26, and is generally referred to as a "reinforcement panel". The reinforcement panel 28 may be an absorbent multi-layered nonwoven fabric including one or more layers of a film. The reinforcement panel 28 may be hydrophilic or hydrophobic, and may be chemically treated to achieve a desired absorbency property. In a particular embodiment, the reinforcement panel 28 is a spunbond layer attached to a middle layer of a meltblown material, which is further attached to a backing layer of impervious film. This configuration allows for reinforcement of the first sheet portion 16 around the fenestration opening 26, provides fluid absorption, and ensures a fluid impervious barrier.

As known in the art, the drape 10 may also include an adhesive area or strip on the patient facing surface 24 generally surrounding the fenestration 26. This adhesive may be used to attach the drape to the patient at the surgical site and establish a sterile field within the area define by the tape.

It should be appreciated that the drape 10 may be formed entirely of the base sheet material discussed above without an additional reinforcement panel, or the drape 10 may be formed entirely of a material corresponding to the reinforcement panel material.

A second sheet portion 30 is attached to the lower or patient facing surface 24 of the first sheet portion 16 along an attachment line or axis 34. The sheet portions may be attached by any conventional means, including adhesive, bonding, welding, stitching, and so forth. The second sheet portion 30 includes an outward facing surface 36 (away from the patient) and a patient facing surface 38 (towards the patient). The second sheet portion 30 has a size and a configuration so as to be draped from the first sheet portion 16, between the patient's legs, and extend under the patient's buttocks while remaining attached to the first sheet portion 16 during the medical procedure, as illustrated in FIG. 1.

In a particular embodiment, the second sheet portion 30 is attached to the first sheet portion 16 at a location above the fenestration (towards the patient's head). The second sheet portion 30 thus includes an opening or axis 32 that is generally alignable with the fenestration 26 such that the medical procedure is performed through the opening 32 in the second drape portion 30. This opening 32 may be defined in various ways. For example, in the embodiment illustrated in FIG. 2, the opening 32 is defined by a perforation line 33 in the material of the second sheet portion 30. A member of the surgical team may remove the perforated portion prior to the procedure in order to define the opening 32 through the second sheet portion 30. In an alternate embodiment illustrated, for example, in FIG. 3, the opening 32 may be a hole or passage that is cut into the second sheet portion 30 by the medical staff prior to the procedure. In still an alternate embodiment, the opening 32 may be pre-cut in the second sheet portion 30. The opening 32 is not limited by its size or shape, so long as adequate access is provided for the surgeon to the surgical site through the second sheet portion 30.

As noted above, the drape 10 includes a first sheet portion 16 and a second sheet portion 30. The first sheet portion 16 includes a first longitudinal end 23 and a second longitudinal end 25. The second sheet portion 30 includes a first longitudinal edge 40 at the attachment line or axis 34 and a second longitudinal edge 41 that defines a longitudinal length of the second sheet portion 30. The second sheet portion 30 is attached to the lower surface 24 of the first sheet portion 16 along the attachment line or axis 34. The first sheet portion 16 includes a first section 18 defined between the first longitudinal end 23 and the attachment line or axis 34 and a second section 20 defined between the attachment line or axis 34 and the second longitudinal end 25. The fenestration 26 is located within the second section 20 of the first sheet portion 16. The second section 20 of the first sheet portion 16 has a longitudinal length that is defined between the attachment line or axis 34 and the second longitudinal end 25. The fenestration 26 in the second section 20 of the first sheet portion 16 registers with the opening 32 in the second sheet portion 30 at the site of the medical procedure.

In some embodiments, such as those illustrated in FIGS. 2-5, the second sheet portion 30 is attached to the lower surface 24 of the first sheet portion 16 along the attachment line or axis 34 along the entire longitudinal edge 40 of the second sheet portion 30. The attachment line or axis 34 is positioned intermediate of the first longitudinal end 23 and the second longitudinal end 25 of the first sheet portion 16. This arrangement permits the second sheet portion 30 to hang from below the first sheet portion 16 in a flat planar T-configuration.

The second sheet portion 30 may be constructed from various materials. For example, the second sheet portion 30 may be made of the same material as the first sheet portion 16, or a different material. In a particular embodiment, the second sheet portion 30 includes an impermeable material layer. For example, the second sheet portion 30 may be formed of a laminate of an absorbent sheet material and a liquid impermeable material, such as a film, with the liquid impermeable material defining the outwardly facing surface 36 and the absorbent material defining the patient facing surface 38.

The second sheet portion 30 may have various shapes and configurations relative to the first sheet portion 16. For example, in the embodiment of FIG. 2, the second sheet portion 30 has a generally rectangular shape with a width generally equal to the width of the first sheet portion 30 such that the attachment location 34 extends across essentially the entire width of the first sheet portion 16. In an alternate embodiment, the second sheet portion 30 has a width generally less than that of the first sheet portion 16, as illustrated in the embodiment of FIG. 3. In this embodiment, the second sheet portion 30 is generally rectangular in shape and is centered relative to the first sheet portion 16.

It may be desired that the second sheet portion 30 have a contoured shape so as to more easily drape between the patient's legs and be disposed under the patient's buttocks without causing undue bunching or gathering of the second sheet portion 30. For example, in the embodiment illustrated in FIG. 4, the second sheet portion 30 has lateral sides 42 defining a generally hourglass shape. This configuration defines a center portion with a relatively narrow width that drapes between the patient's legs, while the portion that extends under the patient's buttocks has a generally wider width.

Figure 5:
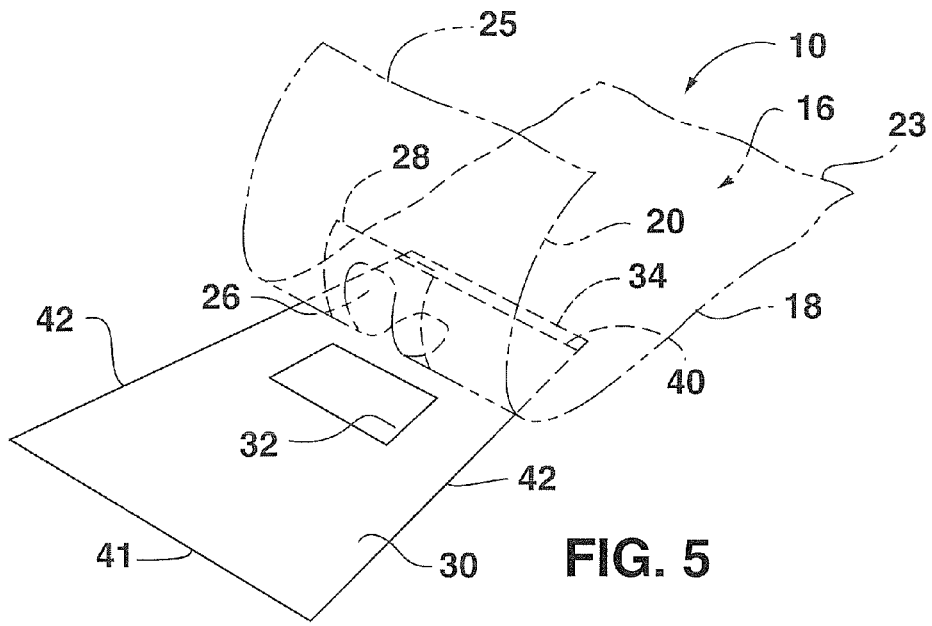
FIG. 5 is a perspective view of another alternative embodiment of an underbuttocks portion of the drape according to the invention.

In the embodiment of FIG. 5, the second sheet portion 30 has tapered lateral side edges 42 that taper from a narrow end attached to the first sheet portion 16 to a wider end that would be tucked under the patient's buttocks.

It should be appreciated that various shapes and configurations of the second sheet portion 30 are within the scope and spirit of the invention.

Figure 6:
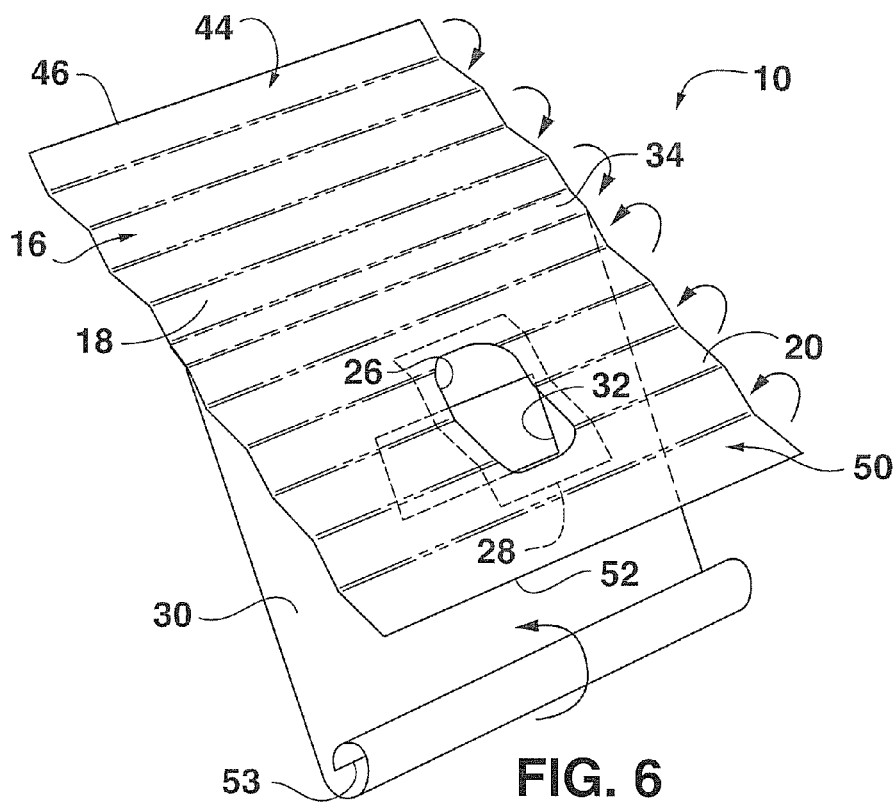
FIG. 6 is a perspective view of an embodiment of the drape illustrating a particular folding and rolled configuration for stowing the drape.
Figure 7:
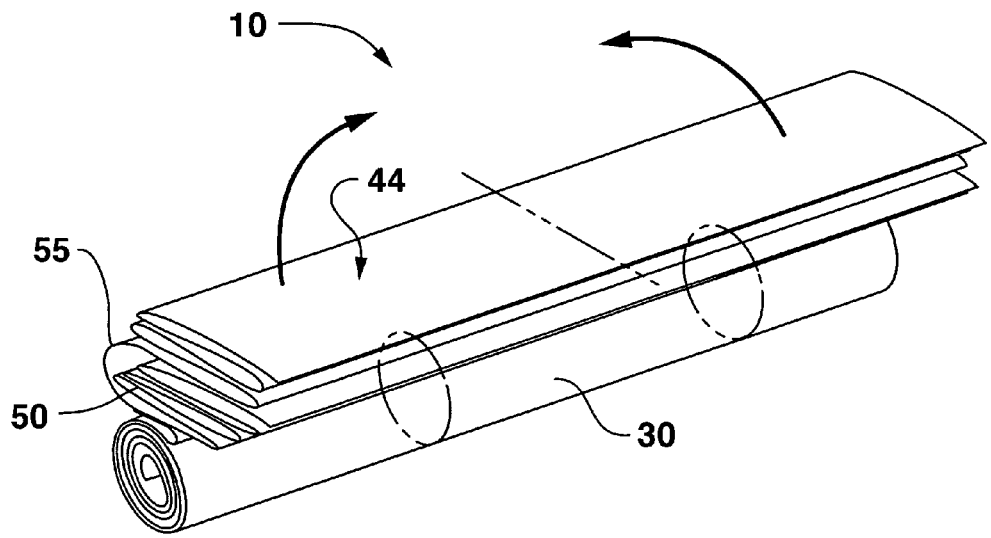
FIG. 7 is a perspective view of the drape of FIG. 6 after being folded and rolled.

The unique drape 10 according to the invention will be presented in a stowed and packaged configuration prior to donning, as is understood in the art. Various configurations and folding patterns may be used to properly stow the drape 10. Preferably, the drape 10 is folded and subsequently unfolded so as to be donned in a single step with minimal medical personnel involvement. In a particular configuration illustrated in FIGS. 6 through 8D, the drape is folded so as to define a first folded section 44 that includes a first section 18 of the first sheet portion 16, and a second folded portion 50 that includes the opposite section 20 of the first sheet portion 16. The sections 18 and 20 are defined by the axis of the attachment 34 between the first sheet portion 16 and the second sheet portion 30, as generally illustrated in FIG. 6. In this configuration, the first section 18 of the sheet portion 16 is folded from a first end 46 towards the attachment access 34, and the second section 20 is folded from its respective end 52 towards the attachment access 34. The second sheet portion 30 is rolled from its respective end 53 towards the attachment access 34. Referring to FIG. 7, the first folded portion 44 may be folded over the second folded section 50 along a line 55 with the rolled second sheet portion 30 disposed generally adjacent to the stacked folded sections 44 and 50, as illustrated in FIG. 7. From this configuration, the drape 10 may be folded inwardly as illustrated by the arrows in FIG. 7 so as to form a compact package that can be subsequently unfolded along the width so as to drape over the patient in an initial position as illustrated in FIG. 8A.

Figure 8A:
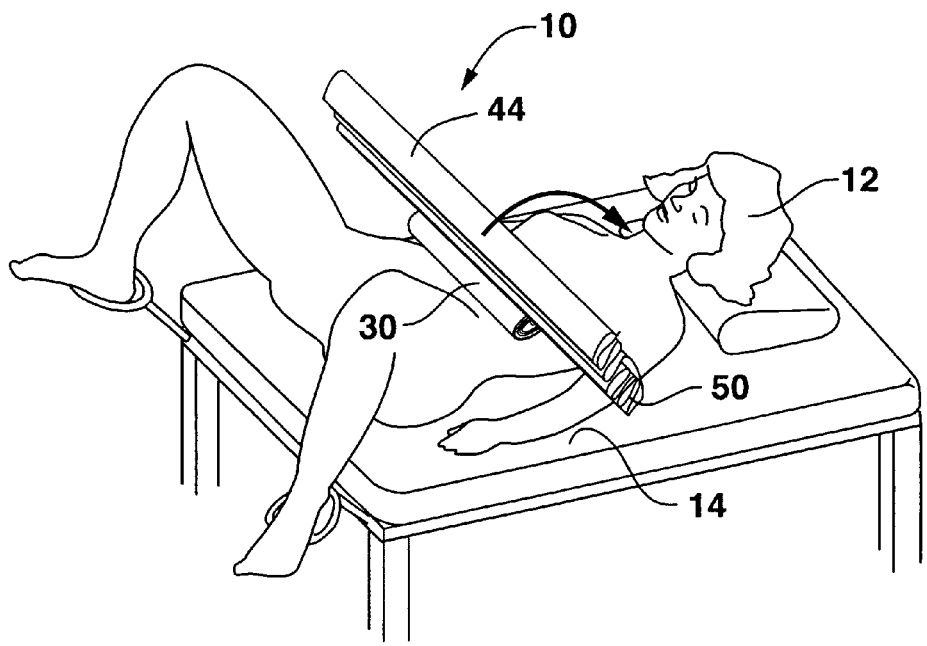
FIGS. 8a through 8d illustrate sequential donning steps for positioning the drape over a patient prior to a medical procedure.
Figure 8B:
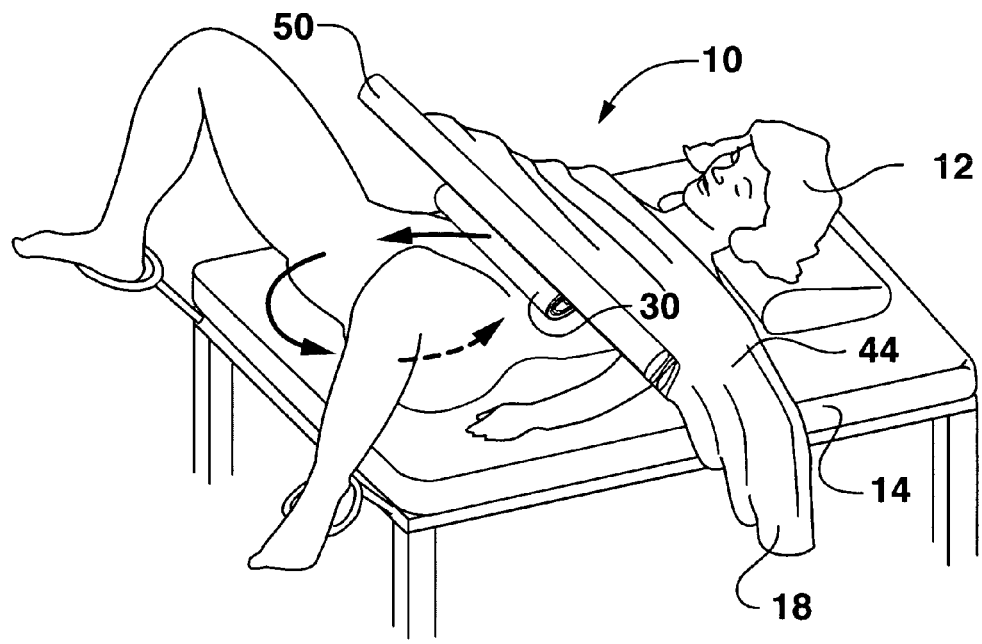
Figure 8C:
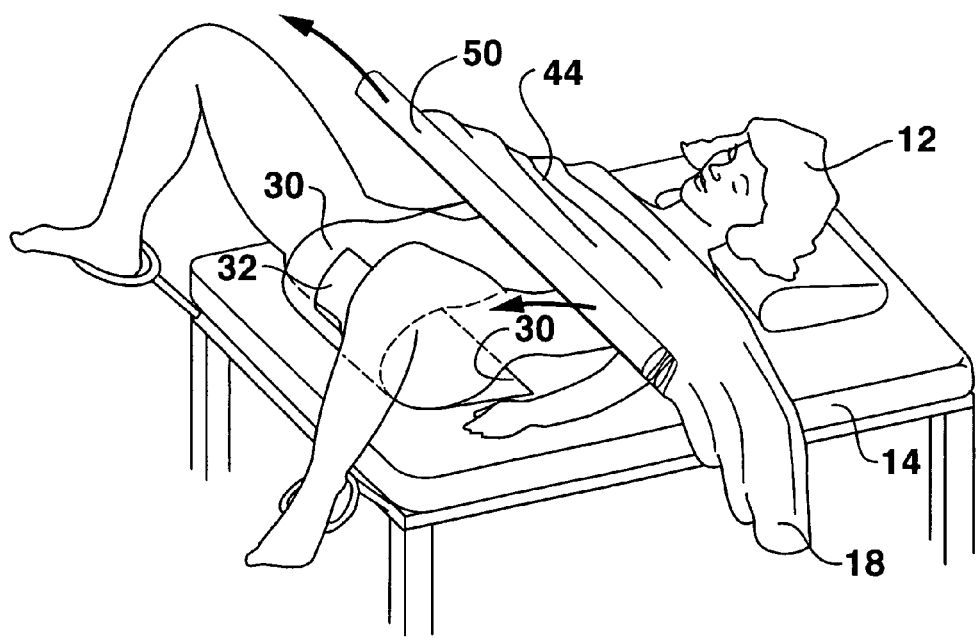

In a donning procedure, from the position of the drape illustrated in FIG. 8A, the first folded section 44 may be unfolded towards the patient's head so that the first section 18 of the drape portion 16 extends generally from the attachment axis 34 over the patient's upper torso, as illustrated in FIG. 8B. At this point, the second sheet portion 30 is positioned between the patient's legs and tucked under the patient's buttocks by being unrolled or unfolded from the attachment axis, as generally depicted in FIG. 8C. The rolled configuration of second section 30 may be desired in that the medical personnel can unroll the sheet portion by placing one's hand and arm within the roll, with the hand and arm remaining covered and sterile during the donning procedure of the drape. Once the underbuttocks portion 30 is properly positioned as illustrated in FIG. 8C, the access opening 32 is defined as discussed above or, if pre-cut, properly positioned at the surgical site.

Figure 8D:
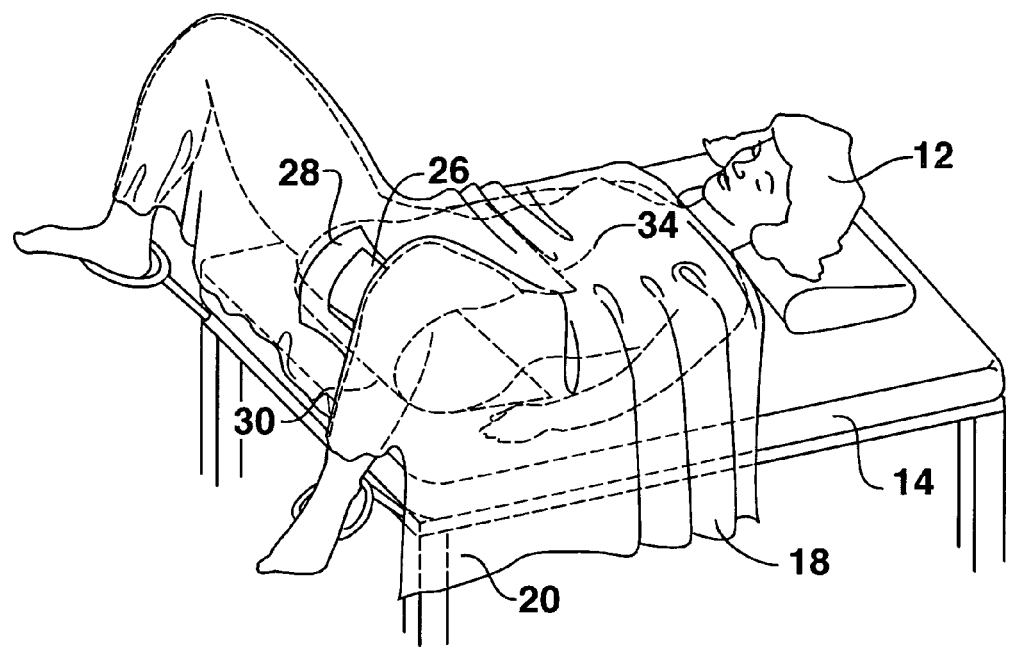

Once the underbuttocks portion 30 has been positioned, the second folded section 50 of the drape portion 16 is then unfolded and draped over the lower torso and legs of the patient, with the fenestration 26 being positioned at the surgical site, as illustrated in FIG. 8D.

It should be appreciated that the folding pattern and sequence described above is but one of any number suitable folding and stowage configurations that may be suitable for donning the drape in an efficient and sterile manner. The drape or its use is not limited to any particular folded configuration or donning process.

It should be appreciated by those skilled in the art that various modifications and variations can be made to the embodiments of the drape illustrated and described herein without departing from the scope and spirit of the invention. It is intended that the invention include such modifications and variations as come within the scope of the appended claims and their equivalents.

What is claimed is:

1. A surgical drape for use during a medical procedure on a patient, comprising:
   a first sheet portion having first and second opposite longitudinal ends and a size and configuration to overlie the patient during the medical procedure, said first sheet portion having an upper surface and a patient facing lower surface;
   a fenestration defined in the first sheet portion at a location corresponding to the site of the medical procedure on the patient;
   a second sheet portion attached to said lower surface of said first sheet portion along an entire longitudinal edge of said second sheet portion along an attachment axis on the lower surface of the first sheet portion that is intermediate of the first and second longitudinal ends of the first sheet portion such that said second sheet portion hangs from below said first sheet portion in a flat planar T-configuration, said second sheet portion having a longitudinal length and configuration sufficient to be draped from said first sheet portion and extend under the patient's buttocks while remaining attached to said first sheet portion during the medical procedure;
   the first sheet portion having a first section defined between the first longitudinal end and the attachment axis, and a second section defined between the attachment axis and the second longitudinal end, with the fenestration in the first sheet portion defined in the second section; and
   an opening defined in the second sheet portion, with the second section of the first sheet portion having a longitudinal length between the attachment axis and the second longitudinal end so as to overly the patient with the fenestration in the second section of first sheet portion registering with the opening in the second sheet portion at the site of the medical procedure.

2. The surgical drape as in claim 1, wherein said second sheet portion comprises a liquid impermeable material.

3. The surgical drape as in claim 2, wherein said liquid impermeable material is at an outwardly facing surface of said second sheet portion, and said second sheet portion further comprises an absorbent material at a patient facing surface thereof.

4. The surgical drape as in claim 3, wherein said second sheet portion comprises a laminate of said absorbent material and said liquid impermeable material.

5. The surgical drape as in claim 1, wherein said first and second sheet portions are formed of a same material.

6. The surgical drape as in claim 1, wherein said second sheet portion comprises a width substantially equal to a width of said first sheet portion and is attached to said first sheet portion across the width of said first sheet portion at the attachment axis.

7. The surgical drape as in claim 1, wherein said second sheet portion comprises a width less than a width of said first sheet portion and is centered relative to said first sheet portion at the attachment axis.

8. The surgical drape as in claim 1, wherein said second sheet portion comprises a generally rectangular shape.

9. The surgical drape as in claim 1, wherein said second sheet portion is non-rectangular in a flat planar state thereof and comprises contoured side edges between the attachment axis and an opposite longitudinal end of the second sheet portion to reduce bunching of said second sheet portion at a location between the attachment axis and the patient's buttocks.

10. The surgical drape as in claim 9, wherein said second sheet portion comprises a generally hour-glass shape.

11. The surgical drape as in claim 9, wherein said second sheet portion diverges from a narrow longitudinal end attached to said first sheet portion to a wider opposite free longitudinal end.

12. The surgical drape as in claim 1, wherein said sheet is in a stowed configuration, said first sheet portion comprising the first section folded from the first longitudinal end towards the attachment axis, and the second section folded from the second longitudinal end in an opposite direction towards said attachment axis, and said second sheet portion being rolled toward said attachment axis.

* * * * *

UNITED STATES PATENT AND TRADEMARK OFFICE
CERTIFICATE OF CORRECTION

| | |
|---|---|
| PATENT NO. | : 7,610,918 B2 |
| APPLICATION NO. | : 11/192441 |
| DATED | : November 3, 2009 |
| INVENTOR(S) | : Bowen et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 549 days.

Signed and Sealed this

Twelfth Day of October, 2010

David J. Kappos
*Director of the United States Patent and Trademark Office*